United States Patent
Moses et al.

(10) Patent No.: US 7,107,997 B1
(45) Date of Patent: *Sep. 19, 2006

(54) METHOD AND APPARATUS FOR INCREASING ANGIOGENIC, GROWTH FACTOR IN HEART MUSCLE

(76) Inventors: Jeffrey Warren Moses, 1175 Park Ave., 12A, New York, NY (US) 10021; Nicholas N. Kipshidze, 345 E. 80th St., Apt. 25B, New York, NY (US) 10021; Martin B. Leon, 875 Park Ave., 12B, New York, NY (US) 10021; Ran Kornowski, 2 Nachai Kidron, Ramat Hasharon, 47314 (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 236 days.

(21) Appl. No.: 10/383,785

(22) Filed: Sep. 9, 2002

Related U.S. Application Data

(63) Continuation-in-part of application No. 09/524,994, filed on Mar. 14, 2000, now abandoned.

(60) Provisional application No. 60/124,643, filed on Mar. 16, 1999, provisional application No. 60/131,485, filed on Apr. 29, 1999.

(51) Int. Cl.
*A61B 19/00* (2006.01)

(52) U.S. Cl. .............................. 128/898; 606/7; 606/9; 607/88; 607/89

(58) Field of Classification Search ................ 128/898; 606/7, 9–15; 607/50, 88–91, 96–101, 103, 607/108, 119
See application file for complete search history.

(56) References Cited

U.S. PATENT DOCUMENTS

| | | | | |
|---|---|---|---|---|
| 5,725,521 | A | * 3/1998 | Mueller | 606/7 |
| 5,989,245 | A | * 11/1999 | Prescott | 606/14 |
| 6,736,808 | B1 | * 5/2004 | Motamedi et al. | 606/15 |
| 6,755,821 | B1 | * 6/2004 | Fry | 606/15 |

* cited by examiner

*Primary Examiner*—A. Farah
(74) *Attorney, Agent, or Firm*—Kajane McManus

(57) ABSTRACT

The present invention relates to methods and apparatuses for use in revascularization of damaged areas of myocardium through application of one or more radiation type treatment modalities.

18 Claims, 1 Drawing Sheet

METHOD AND APPARATUS FOR INCREASING ANGIOGENIC, GROWTH FACTOR IN HEART MUSCLE

CROSS REFERENCE TO RELATED APPLICATIONS

This is a continuation in part of U.S. application Ser. No. 09/524,994 filed on Mar. 14, 2000 now abandoned, bearing the same title which is a continuation of provisional application Ser. No. 60/124,643 filed on Mar. 16, 1999, bearing the same title and provisional application Ser. No. 60/131,485 filed Apr. 29, 1999, bearing the same title.

FIELD OF THE INVENTION

The present invention generally relates to the field of treating myocardial ischemia caused by cardiovascular disease. More particularly, the present invention relates to methods and apparatuses for performing myocardial revascularization and angiogenesis by increasing angiogenic growth in heart muscle.

BACKGROUND OF THE INVENTION

Myocardial ischemia is typically caused by stenosis of one or more coronary arteries. Treatment of this condition can be accomplished by many different techniques, such as coronary bypass surgery, balloon angioplasty, or laser angioplasty. While these treatments are commonly successful, they are not always feasible. For example, a patient may be too frail to withstand the open-heart surgery required for coronary bypass surgery. In addition, if the stenosis is extremely diffuse or totally occluded, angioplasty may not be possible.

Recently, it has been discovered that myocardial ischemia can be treated by forming channels through the myocardium at the location of the ischemia. This procedure is commonly called transluminal myocardial revascularization (TMR). It is theorized that the channels provide oxygenated blood from the left ventricular lumen to the myocardium, thereby alleviating the ischemia. One way of accomplishing TMR is by using a laser or needle to form channels from the exterior of the heart and through the epicardium, myocardium and endocardium. Another way of forming the channels is by percutaneous access through the aorta such that channels can be formed from the inside of the left ventricular lumen. However, recent studies have demonstrated that these channels do not remain patent, and that the major mechanism for long-term success is angiogenesis.

It has been discovered that the above-described TMR technique results in a small amount of angiogenesis (i.e., formation of new blood vessels) in the heart muscle near the formed channels. These new blood vessels enhance the amount of heart muscle that can take advantage of the increased availability of oxygenated blood.

It can be appreciated that it would be advantageous to further promote angiogenesis in damaged heart muscle in order to enhance the availability of oxygen and nutrients to the muscle.

SUMMARY OF THE INVENTION

The present invention is based on the discovery that exposure of smooth muscle cells to low level (e.g., 10 mW–200 mW) electromagnetic radiation (e.g., $10^{24}$ Hz to $10^{11}$ Hz) results in a significant increase (e.g., 40%–50%) in production of vascular endothelial growth factor (VEGF). In addition, in vitro studies have demonstrated that low power laser irradiation (630 nm, 10 mW) increased growth of fetal cardiomyocytes in culture. In the proper environment, increased VEGF results in enhanced angiogenesis. If combined with the TMR procedure, enhanced revascularization can be achieved.

The exposure to radiation can be accomplished directly on the myocardium (e.g., via a laser catheter) or on the epicardium (eg., during open heart surgery). Alternatively, the radiation could be applied without invasive techniques by external exposure (e.g., using a radiation scanner) on the patient's chest in the desired location. The radiation could also be applied from a catheter positioned within an arterial or venous lumen. For example, a venous catheter could be inserted through the coronary sinus and into position within a coronary vein to radiate the heart muscle.

It is anticipated that the required radiation could be produced by a variety of electromagnetic or acoustic sources, such as lasers, ionizing radiation generators, ultrasound generators, etc.

The intensity, wavelength, and duration of the radiation exposure will vary depending on the environment. For example, if radiation is applied directly to the myocardium, low power and long durations may be used, and the exposure could be continuous. On the other hand, if the radiation is applied indirectly on the patient's chest, higher power and short duration will be required. In this latter method, pulsed application of the radiation is preferred to avoid damage to other tissue. Generally speaking in its currently-known preferred embodiment, the radiation wavelength will be between about 400 nm and about 10000 nm, the power will be between about 10 mW and about 2 W, and the duration will be between about 30 seconds and about 10 minutes (continuous mode) and from nanoseconds in pulse mode.

DESCRIPTION OF THE PREFERRED EMBODIMENT

Figure 1:
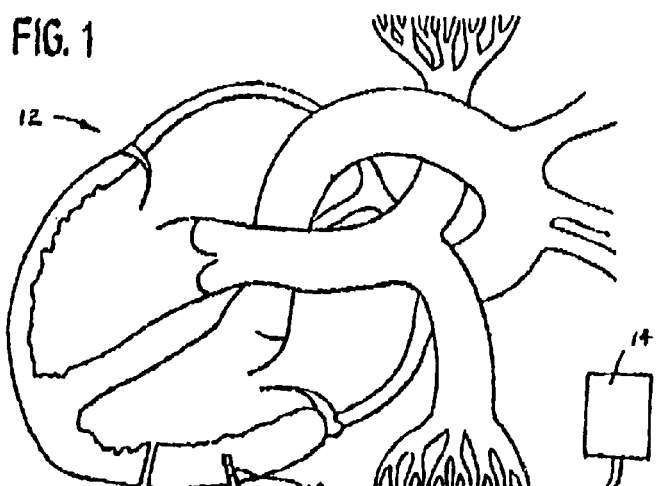
FIG. 1 illustrates a TMR device positioned to perform a TMR procedure from the exterior of the heart and through the epicardium, myocardium and endocardium.
Figure 2:
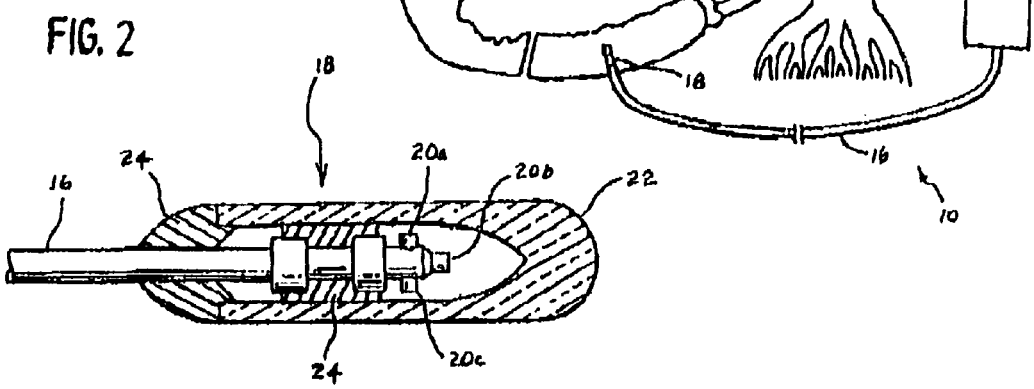
FIG. 2 is an enlarged sectional view of a tip of a TMR device embodying the present invention.

One apparatus for performing direct exposure to the myocardium is illustrated in FIGS. 1 and 2. The apparatus is very similar to known TMR laser devices that emit a high-intensity laser beam at the tip to create the channels for the TMR procedure. For example, a known device is disclosed in U.S. Pat. No. 5,554,152, which is incorporated herein by reference in its entirety. The difference is that the apparatus of the present invention uses relatively low power radiation and is specifically designed to emit radiation or magnetic field radiation or low power ultrasound laterally (i.e., lateral to the longitudinal axis of the catheter tip) into the myocardium surrounding the tip of the device.

Referring to the drawings, one preferred embodiment of the present invention is embodied in a catheter laser device 10 adapted to perform the TMR procedure on a heart 12. In the illustration, the device 10 is performing the TMR procedure from the exterior of the heart, but it should be understood that the practice of the present invention could be performed internally using an aortic catheter, or venous catheter, and also could be performed completely externally of the heart without piercing the heart muscle as well as externally of the body (transcutaneously). It will be understood that when angiogenesis is desired within the heart, access can be obtained either through arterial or venous channels.

Further, it will be understood that the system is equally adapted for use in other organs or even in ischemic lower extremities.

The apparatus in the illustrative preferred embodiment of the Figures includes a laser source 14, an optical fiber 16, and a tip 18. The laser could be a $CO_2$ laser, HO YAG laser, excimer laser, or any other suitable source of radiation such as ionizing radiation or ultrasound, or any other suitable electronmagnetic or acoustic source. Since the present invention is designed to use a low intensity source of radiation, it is anticipated that diode lasers could also be used, thus significantly reducing the cost of the device.

The tip 18 includes multiple radiation outlets 20a, b, c that direct the radiation emanating from the optical fiber 16 in several directions. The illustrated design directs the radiation both axially and radially relative to the axis of the tip 18. This design can be accomplished by providing three separate optical fibers to the three separate outlets 20. If desired, the axial outlet 20b could be provided with a higher intensity radiation compared to the radial outlets 20a, c in order to facilitate formation of the channel in the heart 12.

The tip 18 further includes a lens 22 mounted on the end of the optical fiber 16 using, for example, epoxy 24. The lens 22 can be made from any suitable material, such as quartz. Since the intensity of the radiation delivered by the illustrative device 10 is anticipated to be relatively low, other material, such as plastic, could be used instead.

Figure 3:
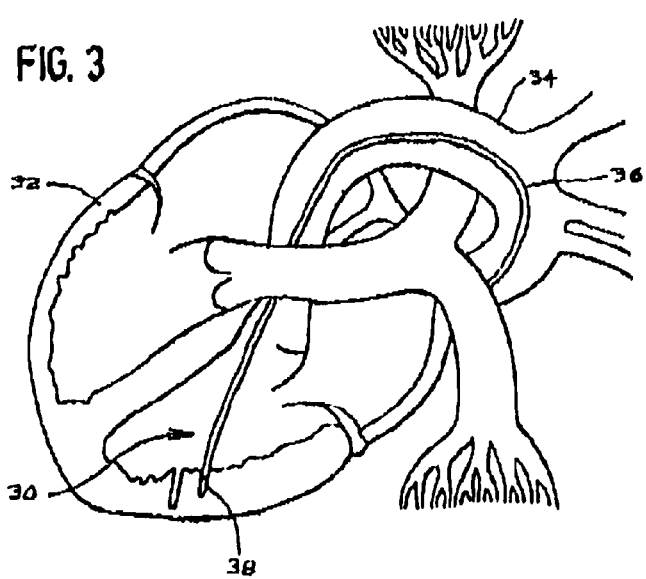
FIG. 3 illustrates one device of the present invention positioned to perform a TMR procedure from the interior of the heart with access via the aorta.

Referring to FIG. 3, another embodiment of the present invention can also be embodied in a device 30 that accesses the heart 32 from the inside via the aorta 34. In this embodiment, the device 30 includes a long catheter 36 that is used to position the tip 38 in the desired position by standard techniques.

With respect to various embodiments using radiation sources as described above, several empirical studies have been performed to date, and exhaustive descriptions of these studies are set forth below.

Photomodulation of Cardiomyocytes with Low-Power Red Laser Light in vitro Condensed Abstract:

The objective of the present study was to determine the effect of LPRLL on proliferation of fetal cardiomyocytes in vitro. All cell cultures were irradiated with single dose LPRLL using a He—Ne continuous wave laser (632 nm) with different energy densities (0.09 to 16.0 $J/cm^2$). Effect of LPRLL on new DNA synthesis was studied by $^3H$ tymidine incorporation assay. VEGF and TGF-â and c-myc mRNA expression by cardiomyocytes was studied by RT-PCR. It was demonstrated that increased cardiomyocyte proliferation can be obtained with LPRLL and this effect is dose dependent. There is two fold increase in VEGF, seven fold increase in TGF-B m RNA expression by cardiomyocites and three fold increase of c-myc m RNA expression by cardiomyocytes. These data may have significant importance leading to the establishment of new methods for myocardial photo-angiogenesis and photo-regeneration.

Abstract

Background and Objective Several reports suggest that low power red laser light (LPRLL) is capable of affecting cellular processes in the absence of significant thermal effect. The objective of the present study was to determine the effect of LPRLL on proliferation of fetal cardiomyocytes in vitro.

DESCRIPTION OF THE PREFERRED EMBODIMENT

One apparatus for performing direct exposure to the myocardium is illustrated in FIGS. 1 and 2. The apparatus is very similar to known TMR laser devices that emit a high intensity laser beam at the tip to create the channels for the TMR procedure. For example, a known device is disclosed in U.S. Pat. No. 5,554,152, which is incorporated herein by reference in its entirety. The difference is that the apparatus of the present invention uses relatively low power radiation and is specifically designed to emit radiation or magnetic field radiation or low power ultrasound laterally (i.e., lateral to the longitudinal axis of the catheter tip) into the myocardium surrounding the lip of the device.

Referring to the drawings, one preferred embodiment of the present invention is embodied in a catheter laser device 10 adapted to perform the TMR procedure on a heart 12. In the illustration, the device 10 is performing the TMR procedure from the exterior of the heart, but it should be understood that the practice of the present invention could be performed internally using an aortic catheter, or venous catheter, and also could be performed completely externally of the heart without piercing the heart muscle as well as externally of the body (transcutaneously). It will be understood that when angiogenesis is desired within the heart, access can be obtained either through arterial or venous channels.

Further, it will be understood that the system is equally adapted for use in other organs or even in ischemic lower extremities.

The apparatus in the illustrative preferred embodiment of the Figures includes a laser source 14, an optical fiber 16, and a tip 18. The laser could be a $CO_2$ laser, HO YAG laser, excimer laser, or any other suitable source of radiation such as ionizing radiation or ultrasound, or any other suitable electronmagnetic or acoustic source. Since the present invention is designed to use a low intensity source of radiation, it is anticipated that diode lasers could also be used, thus significantly reducing the cost of the device.

The tip 18 includes multiple radiation outlets 20a, b, c that direct the radiation emanating from the optical fiber 16 in several directions. The illustrated design directs the radiation both axially and radially relative to the axis of the tip 18. This design can be accomplished by providing three separate optical fibers to the three separate outlets 20. If desired, the axial outlet 20b could be provided with a higher intensity radiation compared to the radial outlets 20a, c in order to facilitate formation of the channel in the heart 12.

The tip 18 further includes a lens 22 mounted on the end of the optical fiber 16 using, for example, epoxy 24. The lens 22 can be made from any suitable material, such as quartz. Since the intensity of the radiation delivered by the illustrative device 10 is anticipated to be relatively low, other material, such as plastic, could be used instead.

Referring to FIG. 3, another embodiment of the present invention can also be embodied in a device 30 that accesses the heart 32 from the inside via the aorta 34. In this embodiment, the device 30 includes a long catheter 36 that is used to position the tip 38 in the desired position by standard techniques.

With respect to various embodiments using radiation sources as described above, several empirical studies have been performed to date, and exhaustive descriptions of these studies are set forth below.

Photomodulation of Cardiomyocytes with Low-Power Red Laser Light in vitro Condensed Abstract:

The objective of the present study was to determine the effect of LPRLL on proliferation of fetal cardiomyocytes in vitro. All cell cultures were irradiated with single dose LPRLL using a He—Ne continuous wave laser (632 nm) with different energy densities (0.09 to 16.0 J/cm$^2$). Effect of LPRLL on new DNA synthesis was studied by $^3$H tymidine incorporation assay. VEGF and TGF-â and c-myc mRNA expression by cardiomyocytes was studied by RT-PCR. It was demonstrated that increased cardiomyocyte proliferation can be obtained with LPRLL and this effect is dose dependent. There is two fold increase in VEGF, seven fold increase in TGF-β m RNA expression by cardiomyocites and three fold increase of c-myc m RNA expression by cardiomyocytes. These data may have significant importance leading to the establishment of new methods for myocardial photo-angiogenesis and photo-regeneration.

Abstract

Background and Objective Several reports suggest that low power red laser light (LPRLL) is capable of affecting cellular processes in the absence of significant thermal effect. The objective of the present study was to determine the effect of LPRLL on proliferation of fetal cardiomyocytes in vitro.

Study Design/Materials and Methods All cell cultures were irradiated with single dose LPRLL using a He—Ne continuous wave laser (632 nm) with different energy densities (0.09 to 16.0 J/cm$^2$). Effect of LPRLL on new DNA synthesis was studied by $^3$H tymidine incorporation assay. VEGF and TGF-â and c-myc mRNA expression by cardiomyocytes was studied by RT-PCR.

Results

It was found that: (i) increased cardiomyocytes proliferation can be obtained with LPRLL and this effect is dose dependent, (ii) there is two fold increase in VEGF and seven fold increase in TGF-â m RNA expression by cardiomyocites, (iii) there is three fold increase of c-myc m RNA expression by cardiomyocytes.

Conclusions: These data may have significant importance leading to the establishment of new methods for myocardial photo-angiogenesis and photo-regeneration.

Introduction

High power laser therapy is a promising intervention in patients with coronary artery disease including transmyocardial laser revascularization for the treatment of end stage coronary artery disease eximer laser assisted angioplasty and selective photodynamic removal of atherosclerotic plaques from vessel wall.

Also, in the past two decades low power laser therapy has gained increased attention in Europe to promote wound healing and tissue repair. Both experimental and clinical studies have demonstrated that low power red laser light (LPRLL) contributes to biomodulation of cellular processes.

The lack of regenerative ability by cardiomyocytes is well recognized and results in loss of contractile function of myocardium due to replacement by fibrotic tissue.

It has been previously demonstrated that LRLL promotes growth of endothelial cells and enhances vascular healing following balloon angioplasty and/or stenting in in vitro animal models.

It has been questioned whether further LPRLL has a similar modulating effect on cardiomyocytes.

The objective of this study was to evaluate the effect of LPRLL on growth of fetal cardiomyocytes in vitro.

Materials and Methods

Fetal cardiomyocyte isolation and culture: Human cardiomyocytes were obtained from Clonetics (San Diego, Calif.) and were grown and maintained in medium SmBM (Biowhitaker, San Diego, Calif.) containing 10% fetal bovine serum at 37° C. in a 5% $CO_2$ and 95% air atmosphere. After 72 hours of culture, cells were trypsinized, washed with medium and counted as described.

Cardiomyocyte proliferation: Cells (1,000,000) were added to each well of a 24 well plate (Primaria, N.J.), and the cells were allowed to grow for 24 hours at 37° C. in a 5% $CO_2$–95% air atmosphere, last 4 hours in the presence of $^3$H thymidine. The cells were washed twice with cold PBS, fixed with cold methanol (95%) and 0.5 ml 0.2 M NaOH were then added to each well and plates stored at 4° C. for 30 minutes. The contents of each well were then transferred to liquid scintillation vials and 3H thymidine uptake was quantified as counts per minute(cpm) using a liquid scintillation counter.

PCR: Total RNA was isolated from cardiomyocytes which were untreated or treated with laser using Trizol (Gibco, Long Island, N.Y.) and quality of RNA verified by the 260/280 nm ratio. 1 μg of RNA was reverse transcribed to cDNA using Ready-To-Go You-Prime-First-Strand beads and oligo dT primers (Phamacia-biotech, USA). The amplification by polymerase chain reaction (PCR) was carried out using 10 μl of cDNA, using Ready-To-Go PCR beads (Pharmacia-biotech, USA) and 2 μl each of 2.5 mM coding and non-coding oligonucleotide primers. The primers sequences were TGF-β:coding 5'-GAA GCG GAA GCG CAT CGA GG-3' (SEQ ID NO:1); noncoding 5'-TCC ACG GCT CAA CCA CTG CC-3' (SEQ ID NO: 2); β-actin: coding 5'-TGA CGG GGT CAC CCA CAC TGTGAA CAT CTA-3' (SEQ ID NO: 3); noncoding 5'-CTT GAA GCA TTT GCG GTG GAC GAT GGA GGG-3' (SEQ ID NO: 4); VEGF: coding 5'-ACC ATG AAC TTT CTG CTG TC-3' (SEQ ID NO: 5); noncoding 5'-TCA CCG CCT CGG CTT GTC AC-3' (SEQ ID NO: 6; c-myc: coding 5'-AAG GAC TAT CCT GCT GGC AA-3' (SEQ ID NO: 7) and noncoding 5'-GGC CTT TTC ATT GTT TTC CA-3' (SEQ ID NO: 8). The PCR amplification profile consisted of 95° C. for 45 seconds, 60° for 45 seconds 72° for 75 seconds. Amplification for TGF-β, p21, coding 5'-AGG ATC CAT GTC AGA ACC GGC TGG-3 (SEQ ID NO 9); noncoding 5-CAG GAT CCT GTG GGA TTA GGG-3 (SEQ ID NO 10). c-myc and VEGF and β-actin was carried out for 32,33,33,32 and 27 cycles respectively. The PCR products were resolved in 1% agarose gel electrophoresis, ethidium bromide stained specific brands were visualized under UV light and photographed. The densitometric analysis of the specific bands was accomplished using Flourimager (Molecular devices, CA, USA0). The data is presented as the ratio of specific gene with the house keeping gene β-actin.

Laser irradiation system. Low power (0–15 mW) Helium-Neon continuous wave (632 nm) laser (Hughes Aircraft Co., model no. 323M-C) was used in this study. Laser irradiation was transmitted from the laser to the cell cultures using 600 micron optical fibers. Laser irradiation experiments were performed at constant energy level of 5 Mw. Exposure time of laser irradiation were 0, 5, 10, 15 and 20 minutes. The cells were kept in a standard air/$CO_2$ incubator that was filled with humidified air containing $CO_2$ before an irradiation session. The temperature of the incubator was kept at 37° C.

The inner walls and bottom of the incubator were black anodized, so light reflections were minimized. No scattering light at the site of the other non-treated wells could be detected in these experiments. Control cells were placed in the field of laser irradiation with opaque covers for the same length of time as the cells receiving laser treatment. No detectable heat was produced during irradiation experiments. After irradiation, cultures were incubated as previously indicated for each experiment. The total power output of the laser beam was determined by a power meter. Statistical evaluation. Resulting values are expressed as the relative number of cells per well compared with initial seeded densities. Cell numbers were averaged for experiments performed under similar conditions and expressed as the mean SD. The statistical significance of differences in the results was evaluated by use of unpaired ANOVA, and a value of $P<0.05$ was accepted as statistically significant.

Results

Cardiomyocyte Proliferation:

Fetal cardiomyocytes were treated with four different doses of LPRLL to determine the growth characteristics. Control cultures displayed a typical growth curve, with a plateau phase when confluency was attached.

Cells treated with LPRLL had an initial rise in cell number one hour following irradiation, but had increase in cell number for 24 hours after treatment ($P<0.05$) compared with control. Stimulating effects on proliferation were most pronounced significantly after irradiation of 10 minutes with laser power of 5 mW ($P<0.05$). Also, it was found that increased expression of VEGF, TGF and c-myc with RT-PCR studies ($P<0.05$ for VEGF; $<0.001$ for TGF and 0.05 for c-myc) as set forth in the following Table.

TABLE 1

THE RATIOS OF TGF-β AND VEGF WITH β-ACTIN.

|  | Control | Laser treated |
|---|---|---|
| TGF-b | 0.28 +− 0.20 | 0.80 +− 0.05 |
| VEGF | 0.08 +− 0.01 | 1.31 +− 0.80 |

Discussion

Effect on Cardiomyocytes

Laser treatment resulted in the increased proliferation of cardiac myocytes. The proliferation was 148±10 percent of control cells without laser treatment. This effect was also dose dependent, since the best effect of proliferation was observed after 10 minute treatment as compared to other treatment doses. Because the mechanism of the laser-induced proliferation of cardiac myocytes is not clear, the expression of transforming growth factor-beta (TGF-β), a multifunctional cytokine that plays a role in cardiac hypertrophy and remodeling was studied. The effects of laser treatment on the expression of vascular endothelial growth factor (VEGF), an angiogenic factor which is involved in vasculature permeability which is increased in response to pulsatile mechanical stretch and hypoxia was also studied. The expression of TGF-β and VEGF mRNA was increased 2–7 fold respectively in laser treated cardiac myocytes. One can hypothesize that the increased proliferation was due to TGF-β induced VEGF mRNA, which has been shown to activate tyrosine and protein kinases resulting in increased cellular proliferation. These data demonstrate that laser induced TGF-β can play a significant role in remodeling and repair of cardiac tissue whereas the induction of VEGF result in the process of angiogenesis in the ischemic heart.

Recently, the concept of enhancing collateral vessel growth in patients not amenable to coronary angioplasty and/or bypass surgery has been introduced and includes the use of various energy sources such as lasers or radiofrequency energy. It may well be that stimulation of VEGF production with LPRLL irradiation is one of the mechanisms of proangiogenic effect of transmyocardial laser revascularization [TLR] and percutaneous transluminal myocardial revascularization [PTMR]. However, the precise mechanism of increased expression of the VEGF gene is unknown. It may be a response to pulsatile mechanical stretch and hypoxia. It is particularly noteworthy that several previous studies have demonstrated light induced vasorelaxation both in vitro and in vivo using UV and visible irradiation from conventional low-power lamps and from lasers. Karlsson et al. and Furchgott and Jothianandan reported in a previous study increased production of cGMP in blood vessels subjected to light treatment and that the level of cGMP correlated with the degree of photorelaxation. It was shown that NAME enhanced photovasorelaxation and it was thought that this response is most likely caused by light induced cleavage of the Nitro group to form NO. NO has been shown as single most critical pro-angiogenic molecule. In vivo studies are underway to explore the LPRLL proangiogenic effect via NO synthesis.

Augmentation of angiogenic genes with LPRLL appears to be nonspecific to the laser irradiation and may be achieved by using other sources of energy at low-power level. Waksman et al., demonstrated increased production of both TGF-β and NO with low dose radiation.

Using catheter based technology, the angiogenic effect of LPRLL is potentially useful as solo therapy or in combination with TLR or PTMR.

Study Limitations:

This study was not without limitations. One of the limitations of the study was the high variability of some of the parameters including cell growth in vitro model. However it should be noted that (i) changes that were observed due to LPRLL action on cell cultures are quite dramatic, (ii) increased expression of growth factors were demonstrated by highly accurate RT-PCR. Another limitation of the study was that fetal cardiomyocytes were studied and effect of LPRLL on diseased or damaged cells is unknown. Finally, the exact mechanism of LPRLL-tissue interaction remains to be established, however, the concept of laser angiogenesis and tissue repair remain appealing.

Conclusion

This study demonstrated that correspondent doses of LPRLL irradiation stimulate cardiomyocyte proliferation, increase in VEGF, TGF-β and c-myc expression.

These data may have significant importance to the establishment of new methods for phototherapy of myocardial healing after injury and promote new vessel growth.

Following is set forth another detailed study.

Biomodulation of Cardiac and Vascular Cells with Low-Power Red Laser light in vitro Abstract background and Objective Numerous reports suggest that low power red laser light (LPRLL) is capable of affecting cellular processes in the absence of significant thermal effect. The objective of this study was to determine the effect of LPRLL on proliferation of fetal cardiomyocytes, human endothelial cells (EC) and smooth muscle cells (SMC) in vitro.

Study Design/Materials and Methods

All cell cultures were irradiated with single dose LPRLL using a He—Ne continuous wave laser (632 nm) with different energy densities. Assessment of effect on cell viability, proliferation and attachment was performed utilizing Alamar Blue assay. Effect of LPRLL on new DNA synthesis was studied by $^3$H thymidine incorporation assay. VEGF secretion by SMC was studied with sandwich enzyme immunoassay technique. VEGF and TGF-β and c-myc mRNA expression by cardiomyocites was studied by RT-PCR.

Results

It was found that: 1) stimulation of cell growth and death can be obtained with LPRLL by varying the energy level, 2) LPRLL increases EC attachment, and 3) cardiomyocytes and EC are more sensitive to photobiomodulation with LPRLL than SMC, 4) increased cardiomyocytes proliferation can be obtained with LPRLL and this effect is dose dependent, 5) there is a two-three fold increase of VEGF secretion by SMC, 6) there is a two fold increase in VEGF and seven fold increase in TGF-β mRNA expression by cardiomyocites, 7) there is a three fold increase of c-myc mRNA expression by cardiomyocytes.

Conclusions

These data may have significant importance leading to the establishment of new methods for myocardial photo-angiogenesis and photo-regeneration.

Introduction

High power laser therapy is becoming more and more common modality in percutaneous cardiovascular interventions, the clinical including transmyocardial revascularization for the treatment of end stage coronary artery disease, eximer laser assisted angioplasty and selective photodynamic removal of atherosclerotic plaques from vessel wall.

In the past two decades low power laser therapy has gained increased popularity in Europe in the treatment of various pathologic processes in humans such as wound healing and tissue repair. A large number of experimental and clinical studies have demonstrated that low power red laser light (LPRLL) contributes to biomodulation of cellular processes.

Recently, LPRLL therapy was implemented for treatment of post-interventional vascular injury, such novel approach found to be effective in inhibiting experimental intimal hyperplasia. While several alternatives has been proposed, this study has focused on investigating the possibility that LPRLL non-specifically stimulates liberation or secretion of growth factors, in particular VEGF in the region around the vascular wall injury. Such effects on endothelium regeneration following coronary interventions are of significant interest because the ability of human endothelium to regenerate is relatively poor.

Vascular endothelial growth factor (VEGF), also known as vascular permeability factor, is a secreted mitogen specific for endothelial cells and an extremely potent angiogenic stimulator. Recent studies have demonstrated that local delivery of VEGF enhances reendothelialization and restores endothelial activity in attached dysfunctional endothelium after balloon mediated injury in rabbits and rats. On the other hand, endothelial cells at the wound edge express a high level of flt-1, one of the two well described high-affinity receptors for VEGF, however, it is interesting to note that significant amounts of this receptor already were seen in the vessel wall several hours after balloon injury. The purpose of these experiments was to investigate the possible VEGF-dependable mechanisms of healing effect LPRLL irradiation on isolated cells derived from vessel wall.

Also, it was reasoned that LPRLL might affect the cellular performance of cardiomyocytes and vascular endothelial and smooth muscle cells in order to photobiomodulate vascular and myocardial tissue, and that the equipment for transmitting the laser irradiation (fiberoptic catheters) to the myocardium or arterial segment is readily available.

The objective of this study was to evaluate the effect of LPRLL on viability, growth, and attachment characteristics of fetal cardiomyocytes and human and rabbit aortic and coronary endothelial (EC) and smooth muscle cells (SMC) in vitro.

Materials and Methods

μgT°CHuman coronary endothelial cell isolation and culture: Human endothelial cells were isolated from coronary vessels (HUC EC) of anonymous donors by collagenase digestion according to previously published methods. After enzymatic treatment and washing with MCDB-131 (Clonetics Corp., San Diego, Calif.), cells were suspended in a medium, supplemented with 7% fetal calf serum and 7% human serum, epidermal growth factor (10 ng/ml), bovine brain extract (36 μg/ml), sodium heparin (1 U/ml), hydrocortisone (1 μg/ml), gentamicin (40 μg/ml) and amphotericin B (250 ng/ml). EC were identified by positive staining for vWF, uptake of florescent acetylated LDL, and by their histotypic "cobblestone" appearance at confluence. HUC EC routinely were grown in supplemented medium MCDB-131, and were used at passages 6–9. Human saphenous vein smooth muscle cells (HSV SMC) were obtained from freshly removed specimens using an explant technique. Briefly, a segment of vein was stripped of fat and connective tissue, then the endothelium was removed by careful stripping, and this segment of vein was chopped into small fragments of approximately 1×1 mm within small volume of DMEM (Hyclone laboratories, Logan, Utah) supplemented with 10% fetal calf serum (Gibco Life Technology Inc., Grand Island, N.Y.) and antibiotic cocktail. The fragments of medial tissue were transferred to a 25 cm$^3$ culture flask, incubated for 2–3 weeks in standard cell culture incubator (VWR scientific, Model 5025) where HSV SMC migrated out of the explants and become subconfluent. Subconfluent cultures were passaged by trypsinization. All cells used for experiments between passages 5 and 7, their growth was characterized by typical "hill and valley" configuration. Normal Human Fibroblasts (HUD FB) were obtained from Clonetics Corp. (San Diego, Calif.) and routinely grown in supplemented medium DMEM. Subconfluent cultures were passaged by trypsinization and used between passages 4 and 8. The number of cells was determined by Alamar Blue assay (Alamar Bio-Sciences, Sacramento, Calif.), which is based on the bioreduction of a flouregenic substrate, the resulting values were converted to cell numbers using standard calibration curves. Individual calibration curves were constructed for each cell type and for each cell medium.

HSV SMC and HUD FB were rendered quiescent replacing their medium with DMEM containing 2% fetal calf serum (serum starved medium) 24 hours before laser irradiation. Alamar Blue assay has shown that this level of serum is sufficient to maintain viability but not stimulate proliferation.

All cultures are ascertained to be free of mycoplasma/acholeplasma contamination by evaluation of culture supernatants from cells grown for two passages in corresponding media, without antibiotics, using a commercial mycoplasma detection kit (Genprobe, Inc., San Diego, Calif.)

Smooth muscle cell isolation and culture. Human aortic smooth muscle cells (HASMC) were isolated from aortas of organ donors ranging in age 18–70 years that were stripped of fat and connective tissue and then the endothelial layer was removed by careful stripping. The medial tissue was cut into 4×4 mm explants and plated on 60 mm Petri culture dishes. The explants were incubated in a standard air/$CO_2$ tissue incubator with Dulbecco's Modified Eagle Medium supplemented with 10% fetal calf serum and antibiotics. The isolated cells were routinely tested using an immunostaining procedure, and passed after treatment for 5 minutes with trypsin/EDTA solution. Cells between passage 4–7 were used for these studies. Fetal cardiomyocyte isolation and culture: Human cardiomyocytes were obtained from Clonetics Corp. (San Diego, Calif.) and were grown and maintained in medium SmBM (Biowhitaker, San Diego, Calif.) containing 10% fetal bovine serum at 37° C. in a 5% $CO_2$ and 95% atmosphere. After 72 hours of culture, cells were trypsinized, washed with medium and counted as described.

Cell quantification: The number of cells plated in each experiment was determined directly by using a standard hemocytometer. After attachment, quantitation of viable cells attached to the substrates was performed by Alamar Blue (AB) assay. AB was added to cell cultures at 1:10 v/v ratio and incubated for 3 hours at 37° C. in the incubator. The fluorescence yield was obtained by measuring in a spectrofluorometer (Model 650-10S, Hitachi, Japan) set at excitation and emission wavelengths of 560 and 590 nm. The resulting values were converted to cell numbers using standard calibration curve.

Cell viability assay: The ability of laser irradiation to affect confluent cell monolayer on polystyrene tissue culture substrate was measured into 96-well Dynatech's pigmented plates. Various doses of irradiation were applied to at least 6 wells in serum containing medium. At the end of irradiation at 37° C., the wells were washed twice with same warm medium to remove any nonviable unattached cells. The viable cells were enumerated by AB assay. Individual experiments were repeated at least three times. Normalized viability index was calculated.

Cardiomyocite proliferation: Cells (1,000,000 cells) were added to each well of a 24 well plate (Primaria, N.J.), and the cells were allowed to grow for 24 hours at 37° C. in a 5% $CO_2$–95% air atmosphere, last 4 hours in the presence of 3H thymidine. The cells were then washed twice with cold PBS, fixed with cold methanol (95%), were washed twice with cold PBS and 0.5 ml 0.2 M NaOH, were then added to each well and plates stored at 4 C for 30 minutes. The contents of each well were then transferred to liquid scintillation vials and 3H thymidine uptake was quantified as counts per minute (cpm) using a liquid scintillation counter.

PCR: Total RNA was isolated from cardiomyocytes which were untreated or treated with laser using Trizol (Gibco, Long Island, N.Y.) and quality of RNA was verified by 260/280 nm ratio. 1 μg of RNA was reverse transcribed to cDNA using Ready-To-Go You-Prime-First-Strand beads and oligo dT primers (Phamacia-Biotech, USA). The amplification by polymerase chain reaction (PCR) was carried out using 10 μl of cDNA, using Ready-To-Go PCR beads (Pharmacia-Biotech, USA) and 2 μl each of 2.5 mM coding and non-coding oligonucleotide primers. The primers sequences were TGF-β:coding 5'-GAA GCG GAA GCG CAT CGA GG-3' (SEQ ID NO: 1); noncoding 5'-TCC ACG GCT CAA CCA CTG CC-3' (SEQ ID NO: 2); α-actin: coding 5'-TGA CGG GGT CAC CCA CAC TGTGAA CAT CTA-3' (SEQ ID NO: 3); noncoding 5'-CTT GAA GCA TTT GCG GTG GAC GAT GGA GGG-3' (SEQ ID NO: 4); VEGF: coding 5'-ACC ATG AAC TTT CTG CTG TC-3' (SEQ ID NO: 5); noncoding 5'-TCA CCG CCT CGG CTT GTC AC-3' (SEQ ID NO: 6); c-myc: coding 5'-AAG GAC TAT CCT GCT GGC AA-3' (SEQ ID NO: 7) and noncoding 5'-GGC CTT TTC ATT GTT TTC CA-3' (SEQ ID NO: 8). The PCR amplification profile consisted of 95° C. for 45 seconds, 60° C. for 45 seconds 72° C. and for 75 seconds. Amplification for TGF-β p21:coding 5'-AGG ATC CAT GTC AGA ACC GGC TGG-3' (SEQ ID NO:9); noncoding 5'-CAG GAT CCT GTG GGC GGA TTA GGG-3' (SEQ ID NO 10); c-myc and VEGF and β-actin was carried out for 32, 33, 33, 32 and 27 cycles respectively. The PCR products were resolved in 1% agarose gel electrophoresis, ethidium bromide stained specific brands were visualized under UV light and photographed. The densitometric analysis of the specific bands was accomplished using Flourimager (Molecular Devices, CA, USA). The data is presented as the ratio of specific gene with the house keeping gene β-actin.

Cell growth and attachment evaluation: EC were seeded onto 96-well Dynatech's pigmented plate at initial density of 10,000 cells/cm$^2$ for evaluation growth rate. After 24 hours, number of cells was indicated by AB assay and EC monolayers were irradiated with various doses of red laser light. Each test-dose was performed in six wells. Quantitation by AB assay was performed for nine days, and refreshment of culture medium was done after each assay.

Confluent cell monolayers were washed briefly with washing buffer then incubated with 0.1% tryspin/0.02% EDTA solution at 37° C. After approximately 3 minutes the cells were displaced from tissue culture flasks into suspension, washed in media, then centrifuged and resuspended in fresh media density 50,000 cells/cm$^2$. Cells were irradiated with various doses of red light and seeded at this density into 24-well plates and incubated for three hours. Cell attachment was quantitated by AB assay after removing nonadherant cells by three cycles of vigorous washes.

Collection of conditioned media: Irradiated cells supplied with fresh serum-starved DMEM were cultured under standard conditions in incubator at 37° C. The samples were harvested 24 hours after cultivation, passed through a Millipore filter (0.2 μm), and then centrifuged (Beckman Microfuge E) at 5,500 g for 10 minutes. The supernatant was frozen and stored at −70° C. until used.

Proliferation assay: To determine the endothelial cell response, HUC EC were placed onto 96-well tissue culture microplates coated with collagen at a density of 2500 cells/well and allowed to attach to the substrate for 24 hours. At the end of this period, the cell density was measured using AB assay and cells were treated with VEGF added to medium or conditioned media. The media were replaced every 24 hours. At this time, total cell density was again calculated and percentage increase in cell density determined. Cell morphology was checked visually via phase-contrast light microscopy after the each 24 hours incubation period to determine the relative health of the culture.

Human VEGF immunoassay: After the cultures were exposed to LPRLL, they were incubated for 24 hours and then the VEGF level in the supernate was measured. For the qualitative determination of the VEGF in cell culture supernate Quantikine™ kit and procedure (R&D System, Inc., Minneapolis, Minn.) were used. This assay employs sandwich enzyme immunoassay technique and monoclonal antibodies specific for VEGF pre-coated onto a microplate. Dilutions of the highly purified VEGF$_{165}$ reagent were used to generate calibration curve for colometric measurement and to stimulate endothelial cells in serum-starved medium. Laser irradiation system: Low power (0–15 mW) Helium-Neon continuous wave (632 nm) laser (Hughes Aircraft Co., model no. 323M-C) was used in this study. Laser irradiation was transmitted from the laser to the cell cultures using 600 micron optical fibers. During laser irradiation the cells were kept in a standard air/$CO_2$ incubator that was filled with humidified air containing $CO_2$ before an irradiation session. The temperature of the incubator was kept at 37° C.

The inner walls and bottom of the incubator were black anodized, so light reflections were minimized. No scattering light at the site of the other non-treated wells could be detected in these experiments. Control cells were placed in the field of laser irradiation with opaque covers for the same length of time as the cells receiving laser treatment. No detectable heat was produced during irradiation experiments. After irradiation, cultures were incubated as previously indicated for each experiment. The total power output of the laser beam was determined by a power meter.

Statistical evaluation: Resulting values are expressed as the relative number of cells per well compared with initial seeded densities. Cell numbers were averaged for experiments performed under similar conditions and expressed as the mean±SD.

Results: Experiments in tissue culture demonstrated that very low levels of laser irradiation were impact on cell growth. In the next series of experiments the effect of LPRLL irradiation on EC and SMC cell growth. The results are shown in FIGS. 5, 6, 7, and 8. Both human and rabbit EC revealed enhanced growth rate and reached confluence faster following laser irradiation with 0.54 J/cm² than control non-irradiated cells. Higher doses of LPRLL, however, decreased cell growth. In contrast, the experiments on SMC revealed that nontoxic doses of LPRLL did not enhance growth rate and there was no difference in comparison with control cultures. Higher doses of LPRLL irradiation were cytotoxic for both EC and SMC and decreased their growth.

Impact on Growth factor expression: The angiogenic response of cultured cells exposed to LPRLL and following a 24 hour incubation is summarized in FIG. 1. Quiescent smooth muscle cells and fibroblasts were capable of producing appreciable amounts of VEGF. Secretion of VEGF was stimulated after 3 minutes LPRLL-exposition and became maximal at exposition time 5 minutes for smooth muscle cells (167.5% of stimulation) and 20 minutes exposition for fibroblasts (162.7% of stimulation). Longer exposition decreased level of VEGF in supernate of smooth muscle cells. These results suggest that both types of cells may be a concentrated local source of diffusible VEGF after laser irradiation and such enhancement is dose dependent. Although there is a difference in maximal dose-response peak of VEGF secretion for each studied cell types.

In subsequent experiments, HSV SMC derived serum-starved conditioned medium would promote replication of endothelial cells in culture was tested. When conditioned medium was added to HUC EC plated into 96-well microplate proliferation of the cells in a such media was a little after C-serum starved media. In contrast, cell growth becomes pronounced at day three when conditioned media was taken from culture treated with LPRLL.

In an additional experiment, it was determined if the different doses of VEGF in the control serum-starved medium incubated with HUC EC would lead to the same quantitative results as those obtained with conditioned medium taken from laser-stimulated cells HUC EC exhibited a significant increase in cell density following a 72 h incubation in a medium containing 5.0 ng of VEGF9, however, the proliferation in control cultures incubated with 2.5 ng/ml VEGF was statistically indistinguishable. For cultures treated with VEGF at concentrations ranging from 10 to 50 ng/ml, the percentage increases in cell density were statistically greater (p<0.001), although there was lowest response (p<0.05) than with laser conditioned medium at optimal stimulation time.

Cardiomyocyte proliferation: Fetal cardiomyocytes were treated with three different doses of LPRLL to determine the growth characteristics. Control cultures displayed a typical growth curve, with a plateau phase when confluency was attached.

Cells treated with LPRLL had an initial rise in cell number one hour following irradiation, but had increase in cell number for 24 hours after treatment (p<0.05) compared with control. Stimulating effects on proliferation were most pronounced significantly after irradiation of 10 minutes with laser power from 5 to 6 mW (p<0.05). Also, noted was found increased expression of VEGF, TGF and c-myc with RT-PCR studies (p<0.05 for VEGF; <0.001 for TGF and 0.05 for c-myc).

Impact on attTDiscussion

Effect on Vascular Cells:

This study demonstrated for the first time that low power red laser light (632 nm) is capable of photobiomodulation of metabolic processes of vascular EC and SMC, showing that stimulation and/or inhibition of cell proliferation in vitro can each be obtained with LPRLL by varying the energy level. In the experiments EC were more sensitive to photobiomodulation with LPRLL then SMC. A therapeutic nontoxic dose of laser irradiation that enhances EC growth but doesn't affect SMC proliferation was identified. SMC were more resistant to LPRLL, however, although a higher dose of LPRLL was cytotoxic for both EC and SMC. These data correlate with other reports. In these studies it is recognized that low power laser is capable of influencing cellular behavior in the absence of significant thermal effect. The biologic mechanisms of low power laser-tissue interaction and clinical effects that stem from these interactions are, however, poorly understood. Inhibition or stimulation of cell growth, differentiation, motility, migration, and phagocytosis are among the effects that have been demonstrated previously in vitro. Despite these observations there is no universally accepted theory as to the mechanisms of laser biomodulation of cellular processes.

Numerous experimental and clinical reports indicate that low power red laser light contributes to tissue repair and regeneration. The studies show that LPRLL increases the attachment efficacy of endothelial cells. Similar results have been reported by Karu et al. demonstrating that LPRLL irradiation improves adhesion characteristics of He—La cells in vitro. These authors speculated that visible light affects the intensity of ion fluxes through the cell membrane, which may enhance cell sedimentation and adhesion. The performance of tumor cells, however, is not strongly dependent upon attachment/adhesion. In contrast, for EC, which are anchoring dependent cells, the process of attachment is crucial. In order to initiate proliferation EC needs attachment and spreading. Without proper attachment desquamed EC will be subjected to apoptosis. It is believed that enhancement of cellular attachment expedites endothelialization and could possibly explain the positive changes in the tensile strength of wounds subjected to LPRLL irradiation.

Effect on cardiomyocites: Laser treatment resulted in the increased proliferation of cardiac myocytes. The proliferation was 148±10 percent of control cells without laser treatment. This effect was also dose dependent, since the best effect of proliferation was observed after 45 minute treatment as compared to 30 minute treatment. Though the laser-induced proliferation of cardiac myocytes is not clear, expression of transforming growth factor-beta (TGF-β), a multifunctional cytokine that plays a role in cardiac hypertrophy, remodeling the repair, was studied. Further studied was the effects of laser treatment on the expression of vascular endothelial growth factor (VEGF), an angiogenic factor which is involved in vasculature permeability and its expression is increased in response to pulsatile mechanical stretch and hypoxia. The expression of TGF-β and VEGF mRNA was increased 2–7 fold respectively in laser treated cardiac myocytes. It is likely that the increased proliferation was due to TGF-β induced VEGF mRNA, which has been shown to activate tyrosine and protein kinases resulting in increased cellular proliferation. These data demonstrate that laser induced TGF-β can play a significant role in remodeling and repair of cardiac tissue whereas the induction of VEGF might result in the process of angiogenesis in the ischemic heart.

Angiogenesis: this study, VEGF was demonstrated to be markedly stimulated in human vascular smooth muscle cells and fibroblasts in vitro in response to LPRLL irradiation. This has created a spatial gradient of VEGF toward denuded area, permitting endothelial cell migration and proliferation. Consistent with this model, LPRLL therapy reduced neointimal hyperplasia in vivo model.

Among the factors that promote angiogenesis and regeneration of endothelium, VEGF is probably the only one that acts exclusively by stimulating directly the endothelium, but not smooth muscle cells or fibroblasts. Recent studies have suggested that VEGF stimulates not only angiogenesis but also endothelial cell regrowth in denuded arteries. Serum levels of VEGF were markedly increased in patients with acute myocardial infarction undergoing acute reperfusion therapy, however, such increase is not enough to stimulate regeneration of endothelium or angiogenesis in ischemic myocardium. Biostimulation via LPRLL may locally blow up levels of cytokines up to 2–5 fold in culture. Thus, selective stimulation could be used in vivo either for angiogenesis or for regeneration of endothelium. Continuos and bolus VEGF infusion had several side effects and low efficiency on endothelial cell regrowth whereas local production of factor in vicinity of injury where flt-1, VEGF receptor is markedly upregulated in the endothelium may lead to expedited regeneration of endothelium and, as a result, of lower restenosis. In addition of promotion of angiogenesis, VEGF alters the pattern of endothelial cell activation, upregulating the expression of plasminogen activators and collagenase. Of particular relevance to this discussion, these enzymes may switch the phenotype of smooth muscle cells. The final inhibitory effects of LPRLL on vascular remodeling and restenosis are dependent upon contact or very close opposition of smooth muscle and endothelial cells. Localization of receptor expression and VEGF secretion suggests a role for this factor in post-interventional healing events.

Endothelial Growth factors produced by the subendothelial vascular cells include bFGF and VEGF, which have been shown to act synergistically in stimulating endothelial cells during vascular wound healing. It also may very well be that this is one of the mechanisms by which laser energy delivered to ischemic myocardium during the procedure of trans-myocardial vascularization enhances angiogenesis. Nevertheless, the simplicity of using LPRLL during interventional procedures to enhance secretion of VEGF into the injured vessel wall as a mechanism of biostimulation is both an exciting and encouraging finding. Further studies will be necessary to identify the entire spectrum of mediators and inhibitors that are synthesized and released by vascular cells in response to LPRLL.

The net stimulatory activity in vivo results from a balance between mediators and inhibitors. In other words, enhanced production of VEGF production does not necessarily equate with stimulation due to a counterbalance of the stimulatory activity by inhibitors. Therefore, this study included a biological assay allowing an estimate of total activity of conditioned serum-starved media on endothelial cell propagation. The aim of such study also was to determine whether LPRLL demonstrates dose dependent effects showing a switch from stimulatory effects to inhibitory activity. To compare proliferation rates of HUC EC in response to conditioned media highly purified VEGF was added into the controls. It was found that VEGF needed to elicit a stimulatory effect in HUC EC at doses beginning at 5.0 ng/ml, which also appears to promote maximal proliferation. Addition of VEGF at 2.5 ng/ml to the conditioned medium led to response which was not demonstrably greater than those of controls, and addition beyond the 10 ng/ml dosage did not appear to significantly further increase the mitogenic response, presumably due to maximal VEGF receptor occupancy.

Mechanism of action: Detailed review of light-cell interactions is beyond the scope of this manuscript. Briefly, it has been speculated that application of laser light at a very low dose promotes the acceleration of electron transfer within some sections of the respiratory chain. Conversely, higher doses result in free radical formation resulting in cell damage. Some recent studies demonstrated that mitochondria and more specifically some kinds of enzymes (e.g., NADH (B-nicotanimde adenine dinucleotide reduced form) and cytochromes) absorb visible light and then vary the mitochondrial energy metabolism.

Finally, the porphyrin hypothesis must be remembered. As demonstrated by some studies, the basis of interaction between low intensity red light and tissues is a complex of photobiological reactions, characterized primarily (when considering its effect on atherosclerotic tissue) by changed porphyrin metabolism. The hypothesis describing the effect of low-intensity red light to porphyrins has been confirmed by experimental studies and has found use in clinical practice in the form of photodynamic therapy based on saturating the body with an excessive amount of substances containing haematoporphyrins (since it was established in experiment that tissue with atherosclerotic lesions tends to absorb haematoporphyrins more readily than normal tissue) with subsequent delivery of red light and singlet oxygen production.

While not dismissing this hypothesis altogether, it is believed that it is very "narrow" to be able to explain all the changes observed during photomodulation. First, it should be noted that in this study the same changes in cells without using exogenous haematoporphyrins or their derivatives was achieved. Moreover, an analysis of literary data showed that there exist 400 some biologically active substances that, just as haemetoporphyrin, react actively on exposure to low intensity light.

Study Limitations:

This study is not without limitations. One of the limitations of the study is the high variability of some of the parameters including cell viability, growth and attachment in vitro model. However it should be noted that (i) changes that were observed due to LPRLL action on cell cultures are quite dramatic, (ii) increased expression of growth factors were demonstrated by highly accurate sandwich immunoassay technique and also by RT-PCR and finally rapid reendothelialization following endoluminal LPRLL irradiation was demonstrated in two animal models. Another limitation of the study is that normal EC and SMC were studied and effect of LPRLL on diseased or damaged cells is unknown. Finally, the exact mechanism of LPRLL-tissue interaction remains to be established, however, the concept of laser angiogenesis and tissue repair remains appealing.

Clinical implications:

There is a large number of patients with distal diffuse coronary artery disease not amenable for PTCA or CABG. Recently, the concept of establishing new vessel growth in this group of patients by local delivery of different growth factors or by mechanical means including local transmyocardial revascularization (TLR) and radiofrequency revascularization were used.

TLR is in clinical use in a number of centers around the world. However, results from the recent studies have been conflicting and clinical importance of this of treatment remains to be established.

Despite very encouraging first clinical experience with local delivery of angiogenic growth factors, it is unknown if new collaterals will have hemodynamic significance. Also, controversy remains regarding the delivery mechanism of growth factors, hence systemic effect is associated with undesirable adverse effects and finally it needs to be proven that a single injection of growth factor can initiate very fine process of new vessel growth.

Therefore the angiogenic effect of LPRLL may be easily used as solo therapy or in combination with TLR or percutaneous transluminal myocardial revascularization (PTMR) using catheter based technology, with modern navigation systems or in conjunction with biological angiogenesis to enhance new vessel growth.

Finally first clinical experience with endoluminal LPRLL therapy as adjunct to intracoronary stenting demonstrated low restenosis rates at six month follow up. Large randomized study is underway to validate endoluminal LPRLL therapy becoming an important adjunctive for reducing restenosis following coronary interventions.

Conclusion

The studies demonstrate that correspondent doses of LPRLL irradiation stimulate cardiomyocyte proliferation, increase in VEGF, TGF-β and c-myc expression, endothelial cell growth and enhance attachment characteristics without altering smooth muscle cell growth and increase production of VEGF by SMC. Higher doses of LPRLL are cytotoxic for all endothelial and smooth muscle cells and cardiomyocytes.

These data may have significant importance to the establishment of new methods for phototherapy of post angioplasty wound repair and contribute to myocardial healing after injury and promote new vessel growth.

Another study is delineated below:

Low-Power Helium-Neon Laser Irradiation Enhances Production of Vascular Endothelial Growth Factor (VEGF) and Promotes Growth of Endothelial Cells in vitro Numerous reports suggest that low power laser irradiation (LPLI) is capable of affecting cellular processes in the absence of significant thermal effect. The objective of the present study was to determine the effect of LPLI on secretion of vascular endothelial growth factor (VEGF) and proliferation of human endothelial cells (EC) in vitro.

Study Design/Materials and Methods:

Cell cultures were irradiated with single different doses of LPLI (Laser irradiance from 0.10 to 6.3 J/cm$^2$) using a He:Ne continuous wave laser (632 nm). VEGF secretion by smooth muscle cells (SMC) and fibroblasts was quantified by sandwich enzyme immunoassay technique. The endothelial cell proliferation was measured by Alamar Blue assay. VEGF and transforming growth factor beta (TGF-E) expression by cardiomyocytes was studied by reverse transcription-polymerase chain reaction (RT-PCR).

Results:

It has been observed that: 1) LPLI of vascular and cardiac cells results in a statistically significant increase of VEGF secretion in culture (1.6-fold for SMC and fibroblasts and 7-fold for cardiomyocytes) and is dose dependent (maximal effect was observed with LPLI Irradiance of 0.5 J/cm$^2$ for SMC, 2.1 J/cm$^2$ for fibroblasts and 1.05 J/cm$^2$ for cardiomyocytes). 2) Significant stimulation of endothelial cell growth was obtained with LPLI treated conditioned medium of SMC (maximal increase was observed with LPLI conditioned medium with irradiance of 1.05 J/cm$^2$ for SMC and 2.1 J/cm$^2$ for fibroblasts.

Conclusions:

The studies demonstrate that low-power laser irradiation increases production of VEGF by SMC, fibroblasts and cardiac myocytes and stimulates EC growth in culture. These data may have significant importance leading to the establishment of new methods for endoluminal post-angioplasty vascular repair and myocardial photo-angiogenesis.

Condensed Abstract:

The objective of the present study was to determine the effect of LPLI on VEGF secretion and proliferation of human endothelial cells (EC) in vitro. All cell cultures were irradiated with different single doses of LPLI using a He—Ne continuous wave laser (632 nm) with different energy densities. Assessment of effect on proliferation was performed utilizing Alamar Blue assay. VEGF secretion by SMC was quantified by sandwich enzyme immunoassay technique. The study demonstrated that LPLI treatment causes significant increase of VEGF secretion by SMC, fibroblasts and cardiac myocytes. Stimulation of endothelial cell growth can be obtained with LPLI conditioned medium in a dose dependent manner. These data may have significant importance leading to the establishment of new methods for post-angioplasty injury repair and photo-angiogenesis.

Introduction

In the past two decades, low-power (low-intensity) laser therapy or biostimulation has gained increased attention in Europe and Asia in the treatment of various pathologic processes such as wound healing and tissue repair. A large number of experimental and clinical studies have demonstrated that low intensity laser irradiation in the visible and infrared region contributes to biomodulation of cellular processes.

Recently, intravascular LPLI has been proposed for the treatment of post-endovascular restenosis. It was found to be highly effective in inhibiting experimental neointimal formation. While several mechanisms including rapid reendothelialization of the treated vessel, have been proposed to explain the anti-restenotic effect, this work has focused on investigating the possibility that LPLI non-specifically stimulates liberation or secretion of growth factors, in particular vascular endothelial growth factor (VEGF) in the region of the vascular injury. This effect would be of particular significance because the ability of endothelium to regenerate is relatively poor and it has been previously shown that accelerated endothelial regeneration may reduce the restenosis rate in an experimental animal.

Vascular endothelial growth factor (VEGF), also known as vascular permeability factor, is a secreted mitogen specific for endothelial cells and an extremely potent angiogenic stimulator. Recent studies have demonstrated that local delivery of VEGF enhances re-endothelialization and restores endothelial activity in attached dysfunctional endothelium after balloon mediated injury in rabbits. The purpose of this experimental study was to investigate the possible VEGF-dependent mechanisms on the healing effect of the corresponding dose LPLI irradiation in vitro.

Materials and Methods

Primary Cell procurement and culturing: Human endothelial cells were isolated from coronary vessels (HuC EC) of anonymous donors by collagenase digestion according to previously published methods. After enzymatic treatment and washing with MCDB-131 (Clonetics Corp., San Diego, Calif.), cells were suspended in a MCDB medium, supplemented with 7% fetal calf serum and 7% human serum, epidermal growth factor (10 ng/ml), bovine brain extract (36 µg/ml), sodium heparin (1 U/ml), hydrocortisone (1 µg/ml), gentamicin (40µ/ml) and amphotericin B (250 ng/ml). Endothelial cells (EC) were identified by positive staining for vWF, uptake of fluorescent acetylated low density lypoprotein, and by their histotypic "cobblestone" appearance at confluence. HuC EC routinely were grown in supplemented medium MCDB-131, and were used at passages 6–9. Human saphenous vein smooth muscle cells (HuSV SMC) were obtained from freshly removed specimens using an explant technique. Briefly, a segment of vein was stripped of fat and connective tissue, then the endothelium was removed by careful stripping, and this segment of vein was chopped into small fragments of approximately 1×1 mm within small volume of DMEM (Hyclone Laboratories, Logan, Utah) supplemented with 10% fetal calf serum (Gibco Life Technology Inc., Grand Island, N.Y.) and an antibiotic cocktail. The fragments of vascular medial tissue were transferred to a 25 cm$^3$ culture flask, incubated for 2–3 weeks in standard cell culture incubator (VWR Scientific, Model 5025) where HuSV SMC migrated out of the explants and become subconfluent. Subconfluent cultures were passaged by trypsinization. HuSV SMC cells used for experiments were between passages 5 and 7; their growth was characterized by typical "hill and valley" configuration. Normal human dermal fibroblasts (HUD FB) were obtained from Clonetics Corp. (San Diego, Calif.) and routinely grown in supplemented medium DMEM. Subconfluent cultures were passaged by trypsinization and used between passages 4 and 6.

The number of cells was determined by Alamar Blue assay (Alamar BioSciences, Sacramento, Calif.), that is based on the bioreduction of a fluorogenic substrate; the resulting values were converted to cell numbers using standard calibration curves. Individual calibration curves were constructed for each cell type and for each cell medium.

HuSV, SMC and HuD FB were rendered quiescent by replacing their medium with DMEM containing 2% fetal calf serum (serum-starved medium) 24 hours before laser irradiation. Alamar Blue assay has shown that this level of serum is sufficient to maintain viability and constant cell density but not to stimulate proliferation.

All cultures are ascertained to be free of mycoplasma/acholeplasma contamination by evaluation of culture supernatants from each cell type grown for two passages in corresponding media, without antibiotics, using a commercial mycoplasma detection kit (Genprobe, Inc., San Diego, Calif.).

Human cardiomyocytes were obtained from Clonetics (San Diego, Calif.) and were grown and maintained in medium SmBM (Biowhitaker, San Diego, Calif.) containing 10% fetal bovine serum at 37° C. in a 95% air atmosphere. After 72 hours of culture, cells were trypsinized, washed with medium, and counted as described elsewhere.

Collection of conditioned media: Non-irradiated and irradiated cells supplied with fresh serum-starved DMEM were incubated under standard conditions in at 37° C. The samples were harvested 24 hours after cultivation, centrifuged (Beckman Microfuge E) at 5,500×g for 10 minutes, passed through a Millipore filter (0.2 µm) and then was frozen and stored at −70° C. until use.

Proliferation assay: To determine the endothelial cell response, HuC EC were placed on to 96-well tissue culture microplates coated with collagen at a density of 2500 cell/well and allowed to attach to the substrate for 24 hours. At the end of this period, the cell density was measured using Alamar Blue assay and cells were treated with different doses of VEGF 165 (R&D System, Inc, Minneapolis, Minn.) added to fresh DMEM medium or with conditioned media after replacement of serum content. The media were replaced every 24 hours. At this time, total cell density was again calculated. Individual experiments were repeated at least three times using five replicates for each experiment. Cell morphology was checked visually via phase-contrast light microscopy after each 24 hour incubation period to determine the relative health of the culture.

Human VEGF immunoassay: After the cultures were exposed to LPLI, they were incubated for 24 hours and then the VEGF levels in the media supernate were measured. For the qualitative determination of the VEGF in cell culture supernate Quantikine™ kit and procedure (R&D System, Inc., Minneapolis, Minn.) were used. This assay employs sandwich enzyme immunoassay technique with monoclonal antibodies specific for soluble isoforms of VEGF and pre-coated microplate. Dilutions of the highly purified VEGF reagent were used to generate calibration curves for colometric measurement and to stimulate endothelial cells in serum-starved medium.

PCR: Total RNA was isolated from cardiomyocytes which were untreated or treated with laser using Trizol (Gibco, Long Island, N.Y.) and quality of RNA verified by the 260/280 nm ratio. 1 microgram of RNA was reverse transcribed to cDNA using Ready-To-Go You-Prime-First Strand beads and oligo dT primers (Pharmacia-Biotech, USA). The amplification by polymerize chain reaction (PCR) was carried out using 10 µl of cDNA, using Ready-To-Go PCR beads (Pharmacia-Biotech, USA) and 2 µl each of 2.5 mM coding and non-coding oligonucleotide primers. The primers sequences were TGF-β: coding 5'-GAA GCG GAA GCG CAT CGA GG-3'; (SEQ ID NO 1): noncoding 5'-TCC ACG GCT CAA CCA CTG CC-33'; (SEQ ID NO 2) β-actin: coding 5'-CTT GAA CGA TTT CTG CTR TC-3' (SEQ ID NO 3); noncoding 5'-TCA CCG CCT CGG CTT GTC AC-3'. The PCR amplification profile consisted of 95 C for 45 seconds, 60 C for 45 seconds 72 C for 75 seconds. Amplification for TGF-β and VEGF and β-actin was carried out for 32, 33 and 27 cycles respectively. The PCR products were resolved in 1% agarose gel electrophoresis, ethidium bromide-stained specific bands were visualized under UV light and photographed. The densitometric analysis of the specific bands was accomplished using Flurimager (Molecular Devices, CA, USA). Some genes are expressed essentially in all types of nucleated cells, and the product of these genes is needed for general function of the cells. Such genes are termed as "house keeping genes". β-actin, GAPDH, cyclophilins are few examples of house keeping genes. In this study, β-actin was used as house keeping gene. The data is presented as the ratio of specific gene with the house keeping gene β-actin.

Laser irradiation system. Low power (0–15 mW) Helium-Neon continuous wave (632 nm) laser (Hughes Aircraft Co., model no. 323M-C) was used in this study. Laser irradiation was transmitted from the laser to the monolayer cell cultures using a 600-micron optical fiber. In all experiments the optical fiber was fixed with a delivery arm that permitted precise positioning of the fiber tip 45 mm in front of the cell monolayer. That allowed the laser beam width of 16 mm. The expansion of the beam area allowed more uniform light intensity at the culture sites. This also corresponded to the diameter of the culture wells of a 24-well microtiter plate (2 $cm^2$). The laser power of 5 mW was constant in all experiments. After beam transmission, expansion and deflection a laser power of 3.5 mW was detected at the site of the plate. The cell cultures were irradiated with a single dose for 0, 1, 3, 5, 10, 15, 20, 30, 40 and 60 minutes. Total energy and irradiance exposure or dose received by cells taking into account transmission losses was in the range of 0,24–14.4 J and 0.1–6.3 $J/cm^2$. These parameters were found earlier to be optimal for enhancement of endothelial cell attachment in vitro, improvement in growth of cardiac myocytes and augmentation of endothelialization rate after balloon injury in a rabbit model. During laser irradiation the cells were kept in a standard air/$CO_2$ incubator that was filled with humidified air containing $CO_2$ before an irradiation session. The temperature of the incubator was kept at 37° C.

The inner walls and bottom of the incubator were black anodized, so light reflections were minimized, as described. No scattering of light to the site of the other non-treated wells could be detected in these experiments using microtiter plates that were placed on photosensitive paper. Control cells were placed in the field of laser irradiation with opaque covers for the same length of time as the cells receiving laser treatment.

The temperature of the cells was measured using a Cromel/Constantan Thermocouple Probe (Omega Engineering, Stamford, Conn.) with an outer diameter of 25.4 microns imbedded into the cell culture. The thermocouple was connected to a model 450/AET, hand-held digital Thermocouple thermometer (Omega Engineering, Stamford, Conn.) with a temperature range of –137° C. to 205° C., and sensitivity of +–0.1 over the entire range. The accuracy of the probe was confirmed against the standard mercury in glass thermometer in a 37° C. water bath.

No detectable heating was produced during irradiation experiments with exposure time of up to 20 minutes. Theoretically it was predicted previously that there would be a maximal 0.3° C. temperature rise, assuming there is no heat loss during irradiation. However, with longer exposure times, i.e., more then 20 minutes heating of the cell culture was detected for about 2,2° C. at 60 minutes of irradiation time. After irradiation, cultures were incubated as previously indicated for each experiment. A power meter (Coherent, Model 212) determined the total power output of the laser beam.

Statistical Analysis. All experiments were repeated at least three times with five parallel measurements in different wells. Resulting values were expressed as the relative number of cells per well compared with initial seeded densities. Cell numbers were averaged for experiments performed under similar conditions and expressed as the mean±SD. The statistical significance of differences in the results was evaluated by use of (Analysis of Variance) ANOVA and Bonferroni using Graph PAD instat software version 1.14 (GraphPAD Software Inc., San Diego, Calif. USA). A value of $P<0.05$ was accepted as statistically significant.

Results

Impact of LPLI on VEGF Expression by SMC and Fibroblasts.

The response of cultured cells exposed to LPLI and following 24 hour incubation is summarized in FIG. 9. Quiescent smooth muscle cells and fibroblasts were capable of producing appreciable amounts of VEGF. A significant secretion of VEGF was observed at three, five, ten and twenty minutes of LPLI treatment in smooth muscle cells and fibroblasts, respectively. Maximal secretion of VEGF was achieved with five minutes of exposure time for smooth muscle cells (167.5% of stimulation when compared to control non-irradiated cells), whereas 20 minutes exposure time was optimal for fibroblasts (162.7% of stimulation when compared to control). Longer exposure decreased the level of VEGF in supernate of smooth muscle cells and fibroblasts.

Effect of LPLI Treated Conditioned Medium on EC Proliferation.

Enhanced secretion of VEGF after LPLI treatment does not signify that this growth factor possesses biological activity. To address this important question, the effect of LPLI treated conditioned medium on the endothelial cell proliferation was studied. As described above, since an increase in the VEGF secretion in SMC and fibroblasts was demonstrated following LPLI treatment at 3, 5, 10, 20 and 5, 10, 20 minutes of LPLI treatment respectively, and conditioned media from SMC and fibroblast cultures 24 hours after LPLI treatment was collected. In subsequent experiments, it was tested whether HuSV SMC or fibroblast-derived serum-starved conditioned medium would promote replication of endothelial cells in culture. The results are shown in FIG. 10 a and b. Stimulation of proliferation of Hu CEC when non-irradiated HUSV SMS conditioned medium was added to the spreaded Hu CEC culture was not observed. In contrast, a dose-dependent increase in the cell density of EC was observed at day three in response to the LPLI treated conditioned medium and was statistically significant when compared with cell density in response to either standard EC medium or conditioned medium derived from non-irradiated cell cultures.

Effect of VEGF Treated Conditioned Medium on EC Proliferation.

In an additional experiment, it was determined if the different doses of VEGF in the control standard medium incubated with HuC EC would lead to the same quantitative results as those obtained with conditioned medium taken from laser-stimulated cells. HuC EC exhibited a significant increase in cell density following a 72 hour incubation in a medium containing 5.0 ng of VEGF, however, the proliferation in control cultures and incubated with 2.5 ng/ml VEGF was indistinguishable. For cultures treated with VEGF at concentrations ranging from 10 to 20 ng/ml, the percentage increases in cell density were statistically greater ($P<0.05$), although there were lower responses ($P<0.01$) than with laser conditioned medium at optimal stimulation time.

Comparison of the Effect of VEGF and LPLI Treated Conditioned Medium from SMC on EC.

Since both LPLI treated conditioned medium and VEGF increase the cell density of EC, their effects were compared. Conditioned medium from LPLI treated SMC caused comparatively more increase in EC cell density than VEGF conditioned medium.

Impact of LPLI on TGF-β and VEGF mRNA Expression.

The mRNA expression of the pro-angiogenic molecules VEGF and transforming growth factor-beta (TGF-β) in cardiomyocytes, which were treated with LPLI and compared with untreated cells was studied. The expression of β-actin was also studied as house keeping genes. The densitometric analysis of the ethidium bromide-stained bands of these genes was performed and the comparison of the intensities of these genes with respect to β-actin was calculated. Laser treatment for 10, 15 and 20 minutes resulted in an increased expression of TGF-β and VEGF compared with untreated cardiomyocytes. The mean±SD (three consecutive experiments) of the ratio of TGF-β and β-actin for control cells was 0.28±0.2 compared to 0.8±0.05 for LPLI treated cardiomyocytes for 15 minutes ($P<0.05$). Similarly, the mean SEM (three consecutive experiments) of the ratio of VEGF and β-actin for control cells is 0.08±0.01 compared to 1.31±0.8 for LPLI treated cardiomyocytes for 15 minutes ($P<0.001$). However this stimulating effect of LPLI was diminished with longer exposure times (30, 40 and 60 minutes).

Discussion

The main finding of the present study is that biologically active VEGF was demonstrated to be markedly stimulated in human vascular smooth muscle cells, fibroblasts and cardiac myocytes in vitro in response to LPLI, although there was a difference in maximal dose-response peak of VEGF production for each studied cell type. In this study, it was shown that stimulation of EC proliferation in vitro can be obtained with LPLI conditioned medium. The SMC and cardiac myocytes were more sensitive to photobiomodulation with LPLI than fibroblasts. The different effect of 630-nm laser irradiation on different cell types may reflect a dose dependency. It appears that a therapeutic nontoxic dose (3.5 mW for 5 to 15 minutes) of visible laser irradiation (630 nm) has been developed (1) that enhances VEGF production in SMC, fibroblasts and cardiac myocytes and expedites endothelial growth in culture in the absence of any significant heat. In contrast, VEGF production was decreased with longer exposure times. This was not surprising, hence previously it was demonstrated that a higher doses of LPLI was cytotoxic for vascular cells. Obviously, fewer cells will produce a lesser amount of VEGF. Fibroblasts, however, were more photoresistant than cardiac myocytes and SMC. Inhibition or stimulation of cell growth, differentiation, motility, migration, and phagocytosis are among the effects of different doses of light at different wavelength that have been demonstrated previously in vitro on other types of cells. The biologic mechanisms of low power laser-tissue interaction, however, is poorly understood.

In contrast to tumor cells, which are not strongly dependent upon attachment/adhesion, EC are anchoring dependent cells and the process of attachment is crucial. In order to initiate proliferation, EC need attachment and spreading and without proper attachment desquamated EC will be subjected to apoptosis. It was previously shown that LPLI increases the attachment efficacy of endothelial cells. Similar results were reported by Karu et al. who demonstrated that monochromatic low-intensity light and He:Ne laser irradiation improves adhesion characteristics of He—La cells in vitro. Numerous experimental and clinical reports indicate that low power red laser light contributes to tissue repair and regeneration. It is speculated that visible light affects the intensity of ion fluxes through the cell membrane, which may enhance cell sedimentation and adhesion. It is believed that enhancement of VEGF production, as observed in this study, along with improvement of the cellular attachment expedites endothelialization and could possibly explain the positive changes in the tensile strength of wounds subjected to LPLI irradiation.

The net stimulatory activity in vivo results from a balance between mediators and inhibitors. Thus, enhanced production of VEGF does not necessarily equate with VEGF activity. Therefore, the study included a biological assay allowing an estimate of total activity of conditioned media on endothelial cell propagation. To compare proliferation rates of HUC EC in response to conditioned media, highly purified VEGF was added to the controls. Addition of VEGF at 2.5 ng/ml to the conditioned medium led to response that was not demonstrably greater than in controls. Doses of at least 5.0 ng/ml were needed to elicit a stimulatory effect in HuC EC, and similar doses (10, 15 ng/ml) appear to promote maximal proliferation. The VEGF dose of 20 ng/ml did not appear to further increase the mitogenic response, presumably due to maximal VEGF receptor occupancy. However, the laser conditioned medium for SMC demonstrated significantly greater proliferation of EC ($P<0.001$), than VEGF conditioned medium. This finding indicates that either LPLI induces the secretion of a more potent form of VEGF or conditioned medium contains some other closely related factor that was increased after LPLI and subsequently affects EC proliferation. Experiments are planned for neutralizing the effect of conditioned medium on cell density by anti-VEGF antibody to further authenticate these findings.

It has been previously demonstrated that the laser treatment resulted in a dose dependent increased proliferation of cardiac myocytes. Because the mechanism of the laser-induced proliferation of cardiac myocytes is not clear, the expression of TGF-β, a multifunctional cytokine that plays a role in cardiac hypertrophy and remodeling was studied. TGF-β is involved in a variety of important cellular functions, including cell growth and differentiation, adhesion, migration, extracellular matrix formation, and immune function. Moreover, its expression is also correlated with angiogenesis. Similarly, TGF-β is believed to stimulate angiogenesis through the up-regulation of VEGF expression, that is thought to be the most potent angiogenic factor. The relative amounts of VEGF produced in response to cytokines such as TGF-β probably contribute significantly to angiogenesis. VEGF secretion might be the product of induction by physiologic concentrations of other growth factors. VEGF is the common pathway of neovascularization.

The effects of laser treatment on the expression of VEGF, an angiogenic factor that is involved in vasculature permeability which is increased in response to pulsatile mechanical stretch and hypoxia was also studied. The expression of TGF-β and VEGF mRNA was increased 2–7 fold, respectively, in laser treated cardiac myocytes. One can hypothesize that the increased proliferation was due to TGF-β induced VEGF mRNA, which has been shown to activate tyrosine and protein kinases resulting in increased cellular proliferation. These data demonstrate that laser induced TFG-β may play a significant role in remodeling and repair of cardiac tissue, whereas the induction of VEGF promotes the angiogenesis in the ischemic heart.

The precise mechanism of increased expression of the VEGF gene is unknown; however, it may be a response to light induced cell hypoxia. If this is the case, pulsed mode of irradiation will perhaps enhance the observed phenomenon. Most importantly, up-regulation of VEGF in experiments occurred at doses too low to result in heating of cell cultures and Heat Shock Protein (HSP) production; hence heat was not detected during low dose irradiation.

Several previous studies have demonstrated light induced vasorelaxation both in vitro and in vivo using UV and visible irradiation from conventional low-power lamps and from lasers. Karlsson et al. and Furchgott and Jothianandan reported increased production of cyclic guanosine monophosphate (cGMP) in blood vessels subjected to light treatment and that the level of cGMP correlated with the degree of photorelaxation. It should be noted that these similar results were achieved using different sources of monochromatic light (lamps and lasers). This may be explained by the fact that a coherent laser beam following its travel through a fiberoptic system and being dispersed by the tissue, becomes noncoherent light.

It has been also demonstrated that N-nitro-L-arginine methyl ester (NAME) enhanced photovasorelaxation. It is hypothesized that this response is most likely caused by light induced cleavage of the Nitro group to form Nitric Oxide (NO). NO, therefore, has been shown as a single most critical pro-angiogenic molecule. In vivo studies are underway to explore the LPLI effect on cGMP synthesis, and its hydrolysis, regulated by release of phosphodiesterase (PDE) isozymes (particularly by PDE-5 and PDE-6) following intravascular LPRLL of rabbit iliac arteries.

Clinical Implications:

Post-Angioplasty Wound Repair:

Among the factors that promote regeneration of endothelium, VEGF is probably the only one that acts exclusively by direct stimulation of the endothelium rather than smooth muscle cells or fibroblasts. Recent studies have suggested that VEGF stimulates not only angiogenesis but also endothelial cell regrowth as well in denuded arteries.

Biostimulation via LPLI may upregulate levels of local cytokines up to 2–5 fold in culture media. Thus, selective stimulation could potentially be used in vivo to accelerate regeneration of endothelium. Indeed, previous experiments in an atherosclerotic rabbit model reported a beneficial impact of endoluminal LPLI with laser-balloon catheter on the restenosis. The favorable influence of endoluminal LPLI also has been verified after stent placement in the coronary artery of domestic cross bred pigs. One of the possible mechanisms of stimulative effect of low power laser irradiation on endothelial reproduction could be enhanced release of the growth factors. This may create a spatial gradient of VEGF toward denuded area following balloon injury, permitting endothelial cell migration and proliferation. Consistent with in vitro and in vivo model, initial clinical experience with endoluminal LPLI therapy as an adjunct to intracoronary stenting demonstrated low restenosis rates at six month follow up.

Pro-Angiogenic Effect of LPLI:

Recently, the concept of enhancing collateral vessel growth in patients not amenable to coronary angioplasty and/or bypass surgery has been introduced and has included the use of various energy sources such as lasers and radiofrequency energy. It may well be that stimulation of VEGF production with laser irradiation is one of the mechanisms of proangiogenic effect of transmyocardial laser revascularization (TLR) and percutaneous transluminal myocardial revascularization (PTMR). It appears however, that augmentation of angiogenic genes with LPRLL is not limited to the laser irradiation and may be achieved by using other sources of electromagnetic or ultrasound energy at low-power level.

Electrical stimulation could also induce angiogenesis. Several reports described improved collateralization in skeletal muscle following electrical stimulation. Indeed, Kanno et al. recently demonstrated that electrical stimulation augmented VEGF mRNA via transactivation of the VEGF gene. They hypothesized hypoxia to be important stimulus for the expression of the VEGF gene. Similarly, Chekanov et al achieved enhancement of capillary growth in the Latisimus Dorsi Muscle of sheep, using electrical stimulation. In another study increased production of both TGF-β and NO with low dose gamma radiation was demonstrated.

The pro-angiogenic effect of LPLI or other types of electromagnetic radiation (electrical current, magnetic field, etc.) or ultrasound may be potentially used as solo therapy or in combination with TLR or PTMR or as a transcutaneous mode of treatment.

Study Limitations:

Limitations of this study include a high variability of the some parameters including cell growth in culture. However, the sandwich enzyme immunoassay and RT-PCR used in the present study are highly accurate. A second limitation is that only a single wavelength of laser irradiation was applied. Therefore, it cannot be concluded if up-regulation of VEGF is specific to the wavelength tested. Finally, the mechanism of LPLI action on living cells needs further investigation and detailed studies are underway to explore the effect of LPLI on mRNA and protein expression in vascular and cardiac cells to compare effects with those of TGF-β, anti-TGF-β antibody, and specific iNOS inhibitors.

Conclusion.

These studies demonstrate that LPLI increases production of VEGF by smooth muscle cells, fibroblasts and cardiac myocytes and stimulates endothelial cell growth in vitro.

These results are encouraging and suggest that the new methods employing endoluminal phototherapy for post angioplasty vascular repair and promotion of collateral growth may be clinically significant. Further studies are needed to identify and characterize the entire spectrum of mediators and inhibitors that are synthesized and released by vascular and cardiac cells in response to low dose electromagnetic radiation.

TABLE 1

Laser parameters
IRRADIATED AREA = 2 cm2
LASER POWER = 5 mW
FINAL POWER ON CELL CULTURES = 3.5 mW

| TIME OF IRRADIATION | | | | | | | | | |
|---|---|---|---|---|---|---|---|---|---|
| 1 min | 3 min | 5 min | 10 min | 15 min | 20 min | 30 min | 40 min | 60 min | |

| TOTAL ENERGY DELIVERED [J] | | | | | | | | | |
|---|---|---|---|---|---|---|---|---|---|
| 0.21 | 0.63 | 1.05 | 2.1 | 3.15 | 4.2 | 6.3 | 8.4 | 12.6 | |

| IRRADIANCE [J/cm$^2$] | | | | | | | | | |
|---|---|---|---|---|---|---|---|---|---|
| 0.10 | 0.31 | 0.52 | 1.05 | 1.57 | 2.1 | 3.15 | 4.2 | 6.3 | |

Low Power Ultrasound Enhancement of the Production of Vascular Endothelial Growth Factor In Vitro It has been previously demonstrated that low power ultrasound enhances production of vascular endothelial growth factor in vitro. It is hypothesized that TLS may induce new collateral growth of ischemic tissue. The object of this study was to investigate the effect of transcutaneous application of low power ultrasound on new collateral growth in rabbit hind-limb ischemia.

After creating bilateral hind-limb ischemia (distal external iliac artery and femoral artery excision), two doses (8 rabbits per dose) of transcutaneous ultrasound (0.4 w/cm$^2$) were applied to rabbit adductor muscle near the site of the excised femoralis artery for 2 (low dose) and 10 (high dose) minutes daily for four weeks. Contralateral site served as control. Angiography and lower limb-calf blood pressure ratio measurement were performed before sacrifice.

After 30 days in the TLS series, 79.1±10.4 (low dose) and 91.7±8.4 (high dose) contrast medium opacified arteries (COAs) were counted crossing grid lines in 30 squares on a grid section vs. 32.2±7.9 in controls (P<0.05). Capillary density was 283.7±24.5 capillaries/mm2 in controls (P<0.001), Both low and high doses of TLS significantly enhanced new collateral growth. TLS may become a simple noninvasive method of treatment for nonoperable hind-limb ischemia.

As described above, the method and apparatus provide a number of advantages, some of which have been described above and others of which are inherent in the invention. Also modifications may be proposed to the teachings herein without departing from the scope of the invention. Accordingly the scope of the invention is only to be limited as necessitated by the accompanying claims.

What is claimed is:

1. A method of treating tissue ischemia in a living organism the method comprising the steps of:
exposing the area of ischemia to low level nonablative mechanical energy applied externally from an energy source in a sufficient amount and for a sufficient period of time to produce angiogenesis and/or tissue regeneration by improving tissue perfusion in the area of ischemia.

2. The method of claim 1 wherein the energy is applied in a continuous manner.

3. The method of claim 1 wherein the energy is applied in a pulsed manner.

4. The method of claim 1 wherein the area of ischemia exists in a myocardium.

5. The method of claim 1 wherein the area of ischemia exists in an extremity.

6. The method of claim 1 wherein the effect of the low level energy treatment may be enhanced by the administration of pharmaceuticals before, during or after treatment.

7. A method of treating ischemia comprising the step of: applying low-level ultrasound energy to an area of ischemia from a point outside the body in an amount of at least 0.001 mW/mm$^2$.

8. The method of claim 7 wherein the ultrasound energy has a frequency of at least 0.0001 Hertz.

9. The method of claim 8 wherein the frequency is preferably about 0.001 Hertz to 30 MHz.

10. The method of claim 8 wherein the ultrasound energy has a pulse width of at least 1 picosecond.

11. The method of claim 8 wherein the ultrasound energy has a flux of at least 0.0001 mJ/mm$^2$.

12. The method of claim 11 wherein the energy preferably has a flux of at least 0.001 mJ/mm$^2$.

13. The method of claim 8 wherein the ultrasound has a pulse width from about 1 nanosecond to 1 hour.

14. The method of claim 8 wherein the ultrasound has peak power from about 0.001 mW to 1000 W.

15. The method of claim 8 wherein the ultrasound is administered at frequency rates from 0.0001 Hertz to 900 KHz.

16. The method of claim 8 wherein the energy flux is between 0.001 to 100 mJ/cm$^2$.

17. The method of claim 7 wherein the ultrasound power is at least about 0.001 W/cm$^2$.

18. The method of claim 17 wherein the ultrasound power is preferably between about 0.2 and 2.0 W/cm$^2$.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: coding primer for TGF-beta1

<400> SEQUENCE: 1
gaagcggaag cgcatcgagg                                            20

<210> SEQ ID NO 2
<211> LENGTH: 20
<212> TYPE: DNA
<213> ORGANISM: Artificial Sequence
<220> FEATURE:
<223> OTHER INFORMATION: non-coding primer for TGF-beta1

<400> SEQUENCE: 2
tccacggctc aaccactgcc                                            20

<210> SEQ ID NO 3
<211> LENGTH: 30
<212> TYPE: DNA
<213> ORGANISM: Artificial Sequence
<220> FEATURE:
<223> OTHER INFORMATION: coding primer for beta-actin

<400> SEQUENCE: 3
tgacggggtc acccacactg tgaacatcta                                 30

<210> SEQ ID NO 4
<211> LENGTH: 30
<212> TYPE: DNA
<213> ORGANISM: Artificial Sequence
<220> FEATURE:
<223> OTHER INFORMATION: non-coding primer for beta-actin

<400> SEQUENCE: 4
cttgaagcat ttgcggtgga cgatggaggg                                 30

<210> SEQ ID NO 5
<211> LENGTH: 20
<212> TYPE: DNA
```

```
<213> ORGANISM: Artificial Sequence
<220> FEATURE:
<223> OTHER INFORMATION: coding primer for VEGF

<400> SEQUENCE: 5
accatgaact ttctgctgtc                                          20

<210> SEQ ID NO 6
<211> LENGTH: 20
<212> TYPE: DNA
<213> ORGANISM: Artificial Sequence
<220> FEATURE:
<223> OTHER INFORMATION: non-coding primer for VEGF

<400> SEQUENCE: 6
tcaccgcctc ggcttgtcac                                          20

<210> SEQ ID NO 7
<211> LENGTH: 20
<212> TYPE: DNA
<213> ORGANISM: Artificial Sequence
<220> FEATURE:
<223> OTHER INFORMATION: coding primer for c-myc

<400> SEQUENCE: 7
aaggactatc ctgctggcaa                                          20

<210> SEQ ID NO 8
<211> LENGTH: 20
<212> TYPE: DNA
<213> ORGANISM: Artificial Sequence
<220> FEATURE:
<223> OTHER INFORMATION: non-coding primer for c-myc

<400> SEQUENCE: 8
ggccttttca ttgttttcca                                          20

<210> SEQ ID NO 9
<211> LENGTH: 24
<212> TYPE: DNA
<213> ORGANISM: Artificial sequence
<220> FEATURE:
<223> OTHER INFORMATION: coding primer sequence for p21

<400> SEQUENCE: 9
aggatccatg tcagaaccgg ctgg                                     24

<210> SEQ ID NO 10
<211> LENGTH: 21
<212> TYPE: DNA
<213> ORGANISM: Artificial Sequence
<220> FEATURE:
<223> OTHER INFORMATION: non-coding primer for p21

<400> SEQUENCE: 10
caggatcctg tgggattagg g                                        21
```